US007473795B2

(12) United States Patent  
Benage

(10) Patent No.: US 7,473,795 B2
(45) Date of Patent: Jan. 6, 2009

(54) BLENDS OF QUINONE ALKIDE AND NITROXYL COMPOUNDS AS POLYMERIZATION INHIBITORS

(75) Inventor: Brigitte Benage, Wolcott, CT (US)

(73) Assignee: Uniroyal Chemical Company, Inc., Middlebury, CT (US)

( * ) Notice: Subject to any disclaimer, the term of this patent is extended or adjusted under 35 U.S.C. 154(b) by 270 days.

(21) Appl. No.: 11/370,691

(22) Filed: Mar. 7, 2006

(65) Prior Publication Data

US 2006/0155140 A1    Jul. 13, 2006

Related U.S. Application Data

(62) Division of application No. 10/363,970, filed on Mar. 7, 2003, now Pat. No. 7,045,647.

(51) Int. Cl.
    *C07C 69/00* (2006.01)
(52) U.S. Cl. ............................ 560/4; 560/205; 548/542; 546/339; 585/3; 585/4; 585/5
(58) Field of Classification Search .............. 560/4, 560/205; 548/542; 546/339; 585/3, 4, 5
    See application file for complete search history.

(56) References Cited

U.S. PATENT DOCUMENTS

| | | | |
|---|---|---|---|
| 2,046,356 A | 7/1936 | Wyler et al. .................. 260/69 |
| 3,163,677 A | 12/1964 | Hoffman et al. ............. 260/583 |
| 3,267,132 A | 8/1966 | Newsom et al. .......... 260/465.9 |
| 3,334,103 A | 8/1967 | Feldman et al. ............. 260/290 |
| 3,372,182 A | 3/1968 | Hoffmann et al. ........ 260/465.5 |
| 3,422,144 A | 1/1969 | Hoffmann et al. ........... 260/570 |
| 3,494,930 A | 2/1970 | Dupeyre et al. .......... 260/294.7 |
| 3,873,564 A | 3/1975 | Schneider et al. ........ 260/309.6 |
| 3,966,711 A | 6/1976 | Rasberger ................ 260/239.3 |
| 3,988,212 A | 10/1976 | Watson ........................... 203/9 |
| 4,003,800 A | 1/1977 | Bacha et al. .................... 203/9 |
| 4,040,911 A | 8/1977 | Bacha et al. .................... 203/9 |
| 4,086,147 A | 4/1978 | Watson ........................... 203/9 |
| 4,105,506 A | 8/1978 | Watson ........................... 203/9 |
| 4,132,602 A | 1/1979 | Watson ........................... 203/9 |
| 4,132,603 A | 1/1979 | Watson ........................... 203/9 |
| 4,182,658 A | 1/1980 | Watson ........................... 203/9 |
| 4,252,615 A | 2/1981 | Watson ........................... 203/9 |
| 4,341,600 A | 7/1982 | Watson ........................... 203/9 |
| 4,362,893 A | 12/1982 | Kurek ......................... 564/410 |
| 4,466,904 A | 8/1984 | Watson et al. ................. 252/402 |
| 4,468,343 A | 8/1984 | Butler et al. ................... 252/403 |
| 4,479,008 A | 10/1984 | Batorewicz et al. .......... 564/433 |
| 4,518,803 A | 5/1985 | Batorewicz et al. .......... 564/410 |
| 4,665,185 A | 5/1987 | Winter et al. ................. 546/184 |
| 4,774,374 A | 9/1988 | Abruscato et al. ............. 585/24 |
| 5,001,171 A | 3/1991 | Bohm et al. .................. 523/206 |
| 5,254,760 A | 10/1993 | Winter et al. ................... 585/5 |
| 5,504,243 A | 4/1996 | Sakamoto et al. ........... 560/205 |
| 5,545,782 A | 8/1996 | Winter et al. ................... 585/5 |
| 5,545,786 A | 8/1996 | Winter et al. ................ 585/435 |
| 5,583,247 A | 12/1996 | Nesvadba et al. ................ 560/2 |
| 5,616,774 A * | 4/1997 | Evans et al. ............. 252/182.18 |
| 5,623,088 A | 4/1997 | Stern et al. ................... 564/112 |
| 5,648,543 A | 7/1997 | Murata et al. ................ 564/410 |
| 5,670,692 A | 9/1997 | Nesvadba et al. .............. 558/71 |
| 5,711,767 A | 1/1998 | Gande et al. ................... 44/423 |
| 5,739,403 A | 4/1998 | Reinartz et al. .............. 564/423 |
| 5,750,765 A | 5/1998 | Nesvadba et al. ............ 560/126 |
| 5,907,071 A | 5/1999 | Arhancet ......................... 585/5 |
| 5,910,232 A | 6/1999 | Hyde et al. ...................... 203/9 |
| 5,912,106 A | 6/1999 | Chang et al. .............. 430/281.1 |

FOREIGN PATENT DOCUMENTS

| | | |
|---|---|---|
| CS | 260755 B1 | 1/1989 |
| EP | 0 178 168 A2 | 4/1986 |
| EP | 0 240 297 A1 | 10/1987 |
| EP | 0 765 856 A1 | 4/1997 |
| FR | 2761060 | 9/1998 |
| GB | 1127127 | 9/1968 |
| HU | 150550 | 9/1963 |
| JP | 45017652 | 6/1970 |
| JP | 49-75541 | 7/1974 |
| JP | 49125315 | 11/1974 |
| JP | 52-133931 | 11/1977 |
| JP | 62187710 | 8/1987 |
| JP | 53-33578 | 12/1993 |

(Continued)

OTHER PUBLICATIONS

Tudos, Inhibition of Radical Copolymerization, Proc. IUPAC, I.U.P. A.C., Macromol. Symp., 28th (1982), 90.
Laszlone et al., A gyokos polimerization kinetikaja, XVIII, Magyar Kemini Folyoirat 72, evf. (1966) 244-48.
Rabek, Katedra Technologii vol. 10, 3rd Edition, (1965), 443-451.
Dukhnenko et al., Preparation of Low Molecular Weight Water Soluble Poly, Journal of Applied Chemistry of the USSR (1976) p. 696.
Misc. Abstracts.
Sidgwick, F.R.S., The Organic Chemistry of Nitrogen, 3rd Edition, 1966, 352-360.
Tanczos et al., Kinetics of Radical Polymerization, Eur. Polym. J. (1982), 18(6), 487-91.
Tanczos et al., Kinetics of Radical Polymerization, Eur. Poolym. J. (1983), 19(3), 225-9.

(Continued)

*Primary Examiner*—Rei-tsang Shiao
(74) *Attorney, Agent, or Firm*—Jaimes Sher

(57) ABSTRACT

Disclosed herein is a method for inhibiting the premature polymerization of ethylenically unsaturated monomers comprising adding to said monomers an effective amount of:
A) at least one nitroxyl compound, and
B) at least one quinone alkide compound having an electron-withdrawing group at the 7-position.

Additionally, a composition is disclosed that comprises:
A) at least one nitroxyl compound, and
B) at least one quinone alkide compound having an electron-withdrawing group at the 7-position.

9 Claims, No Drawings

FOREIGN PATENT DOCUMENTS

| | | |
|---|---|---|
| RU | 2039757 | 7/1995 |
| SU | 202125 | 2/1968 |
| SU | 478838 | 7/1975 |
| SU | 509604 A | 4/1976 |
| SU | 334845 A1 | 1/1984 |
| WO | 97/46504 | 12/1997 |
| WO | 98/14416 | 4/1998 |
| WO | 98/25872 | 6/1998 |
| WO | 99/20584 | 4/1999 |

OTHER PUBLICATIONS

Tanczos et al., Kinetics of Radical Copolymerization, Eur. Polym. J. (1983), 19(2), 153-7.

Georgieff, Relative Inhibitory Effect of Various Compounds on the Rate of Polymerization of Methyl Methacrylate, J. Appl. Polymer Sci, (1965), 9(6):2009-12.

Zaitsev et al., Use of Stable Free Radicals to Inhibit the Copolymeriation of Vinyl Monomers, Dopov. Akad. Nauk Ukr. RSR, Ser. B:(1977), (11), 988-91.

Georgieff, Relative Inhibitory Effect of Various Compounds on the Rate of Polymerization of Methyl Methacrylate, Journal of Applied Polymer Science. vol. 9, (1965), 2009-2018.

Boguslavaskaya, Comparative Evaluation of the Inhibiting Activity of Variou Compounds in Respect to Acrylic and Methacrylic Monome, Khimicheskaia Promyshlennost, (1967), 29-32.

Tanczos et al., Investigation of Molecule-Inhibitors in the Radicall Polymerization of Methyl Acrylate, Euro. Pol. Journal (1982), vol. 18, 295-99.

Tanczos et al., Investigation of the Effect of Molecule Inhibitors in Copolymerization, Euro. Poly. Journal (1983), 19(7), 593-95.

Kende et al., Investigation of the Effect of Nitroso Compounds on Free Radical Polymerization, Eur. Pol. Journal. (1972), vol. 8, 1281-89.

Gyongyhalmi et al., Kinetics of Radical Polymerization, Eur. Poly. J. (1994), 30(12) 1457-59.

Tudos et al., Kinetics and Mechanism of Polyreactions, Int. Symp, Mecromol. Chem., Prepr., (1969) 5(25): 109-113.

Yoneda et al., Radical Polymerization of Styrene in the Presence of Aromatic Nitroso Compounds, (1970) 27(300), 269-75.

* cited by examiner

BLENDS OF QUINONE ALKIDE AND NITROXYL COMPOUNDS AS POLYMERIZATION INHIBITORS

This application is a divisional of U.S. patent application Ser. No. 10/363,970, filed on Mar. 7, 2003 now U.S. Pat. No. 7,045,647.

BACKGROUND OF THE INVENTION

1. Field of the Invention

The present invention is directed to the use of a combination of at least one quinone alkide and at least one nitroxyl compound to inhibit the polymerization of ethylenically unsaturated monomers.

2. Description of Related Art

Many ethylenically unsaturated monomers undesirably polymerize at various stages of their manufacture, processing, handling, storage, and use. A particularly troublesome problem is equipment fouling caused by polymerization in the purification stages of the production processes of such monomers. Polymerization, such as thermal polymerization, during their purification results in the loss of the monomer and a loss in production efficiency owing to the deposition of polymer in or on the equipment being used in the purification, the deposits of which must be removed from time to time. Additionally, the formation of soluble polymer leads to loss of monomer, i.e., a lower yield, and an increase in the viscosity of any tars that may be produced. The processing of the tars then requires higher temperature and work (energy cost) to remove residual monomer.

A wide variety of compounds has been proposed and used for inhibiting uncontrolled and undesired polymerization of ethylenically unsaturated monomers. In particular, there is a need for an inhibitor that not only provides highly effective inhibition of polymerization during normal operation of a continuous manufacturing or purification process, but also provides satisfactory protection in the event of a loss of continuous inhibitor feed. While many inhibitors are known to provide sufficient protection in one of these scenarios, these inhibitors have not been fully satisfactory under both normal and upset operating conditions. Accordingly, there has been a substantial need in the art for improved compositions for inhibiting the polymerization of such monomers during their production and the distillation process for purifying or separating them from impurities, as well as during transport and storage.

Quinone methides and nitroxyl compounds are known polymerization inhibitors.

Quinone methides act mainly as retarders, giving a significant amount of polymer during normal inhibition usage, but providing protection in the event of a plant upset during monomer purification by slowing the rate of polymer formation under static conditions. Because of the poor normal inhibition performance, quinone methides must be used in fairly high dosages, making them not very economical to use.

U.S. Pat. Nos. 4,003,800 and 4,040,911 disclose the use of quinone alkides in a styrene purification process.

The following patents, assigned to Ciba-Geigy Corporation or Ciba Specialty Chemicals Corporation, relate to quinone methides and uses thereof.

U.S. Pat. Nos. 5,583,247; 5,670,692; and 5,750,765 disclose the protection of ethylenically unsaturated monomers from premature polymerization during manufacture and storage by the incorporation therein of an effective stabilizing amount of a quinone methide compound having an electron withdrawing substituent at the 7-methylene group.

U.S. Pat. No. 5,616,774 discloses the protection of ethylenically unsaturated monomers from premature polymerization during manufacture and storage by the incorporation therein of an effective stabilizing amount of a 7-aryl quinone methide compound wherein the 7-aryl substituent is 2-, 3- or 4-pyridyl, 2- or 3-thienyl, 2- or 3-pyrryl, 2- or 3-furyl, aryl of 6 to 10 carbon atoms, or said aryl substituted by one to three alkyl of 1 to 8 carbon atoms, alkoxy of 1 to 8 carbon atoms, alkylthio of 1 to 8 carbon atoms, alkylamino of 1 to 8 carbon atoms, dialkylamino of 2 to 8 carbon atoms, alkoxycarbonyl of 2 to 8 carbon atoms, hydroxy, nitro, amino, cyano, carboxy, aminocarbonyl, chloro, or mixtures of said substituents. The combination of these quinone methides with at least one stable nitroxyl compound is also disclosed.

U.S. Pat. No. 5,912,106 discloses a method of improving the quality and resolution of photoimages by incorporating into the photocurable resin composition to be used a selected amount of a polymerization inhibitor so that photopolymerization of the photocurable resin is inhibited in those areas not directly impinged by light. Inhibitors that can be used are selected from the group consisting of N-oxyl or nitroxide compounds, quinone methides, nitroso compounds, phenothiazine and selected phenols.

Hindered nitroxyl compounds are known to be very active inhibitors of free radical polymerizations of unsaturated monomers such as styrene, acrylic acid, methacrylic acid, and the like.

U.S. Pat. No. 3,163,677 discloses N,N,O-trisubstituted hydroxylamines and N,N-disubstituted nitroxides of the formulae:

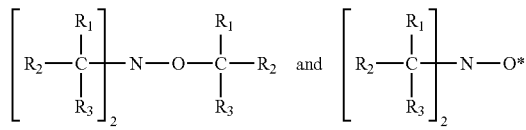

wherein $R_1$, $R_2$, and $R_3$ are each an alkyl radical having 1 to 15 carbon atoms. (As used herein, the designation N—O* denotes a stable free radical wherein the asterisk is an unpaired electron.) The N,N,O-trisubstituted hydroxylamines can be used to make the N,N-disubstituted nitroxides, which are stable free radicals and are said to be useful as polymerization inhibitors.

U.S. Pat. No. 3,334,103 discloses that nitroxides can be prepared from the corresponding heterocyclic amine wherein the nitrogen atom of the nitroxide group is attached to other than a tertiary carbon of an aliphatic group (i.e., the nitrogen atom forms a part of a heterocyclic nucleus). These nitroxides are said to have useful properties similar to those described for the N,N-disubstituted nitroxides of U.S. Pat. Number 3,163,677.

U.S. Pat. No. 3,372,182 discloses that a great variety of N,N-disubstituted, stable, free radical nitroxides not otherwise readily available can be prepared by a simple and convenient process that comprises pyrolyzing in an inert reaction medium virtually any hydroxylamine that is susceptible to cleavage of the O—C bond, e.g., tri-t-butylhydroxylamine.

U.S. Pat. No. 3,422,144 discloses stable, free radical nitroxides of the formula:

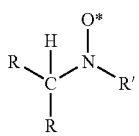

wherein R is selected from the group consisting of tertiary alkyl, aryl, alkaryl, haloaryl, carboxyaryl, alkoxyaryl, alkylthioaryl, pyridyl, and dialkylaminoaryl, and R' is tertiary alkyl. These nitroxides are said to be useful as traps for reactive free radicals both in the counting of free radicals and for inhibiting oxidation and free radical polymerization.

U.S. Pat. No. 3,494,930 discloses free radicals of the nitroxide type for use as initiators of free radical reactions, collectors of free radicals, polymerization inhibitors or antioxidants. They are constituted by nitrogenous bicyclic compounds in which one of the bridges comprises solely the nitroxide radical group and, in particular, by aza-9-bicyclo (3,3,1) nonanone-3-oxyl-9, and by aza-9-bicyclo (3,3,1) nonane oxyl-9.

U.S. Pat. No. 3,873,564 discloses compounds and a method for assaying enzymes by adding to a medium containing an enzyme a stable free radical compound having a stable free radical functionality which, when subjected to an enzyme-catalyzed reaction, changes the environment of the free radical functionality. By following the change in the electron spin resonance spectrum as affected by the change in environment, the type of enzyme and the activity of the enzyme can be determined.

The compounds found useful are normally stable nitroxide radicals with an enzyme labile functionality. Other compounds include two cyclic nitroxide containing rings joined by a chain having an enzyme labile functionality.

U.S. Pat. No. 3,966,711 teaches that 2,2,7,7-tetraalkyl- and 2,7-dispiroalkylene-5-oxo-1,4-diazacycloheptanes substituted in the 4-position by mono- or tetravalent radicals are powerful light-stabilizers for organic polymers. They are said to possess higher compatibility than their 4-unsubstituted homologues, from which they can be synthesized by reactions known for N-alkylation. Preferred substituents in the 4-position are alkyl, alkylene, alkenyl, aralkyl, and esteralkyl groups. The 1-nitroxyls derived from the imidazolidines by oxidation with hydrogen peroxide or percarboxylic acids are also said to be good light stabilizers.

U.S. Pat. No. 4,182,658 discloses a method for preventing the polymerization of a readily polymerizable vinyl aromatic compound during distillation at elevated temperatures within a distillation apparatus that is subject to an emergency condition, such as a power outage. This method comprises force-feeding a supplemental polymerization inhibitor having a high solubility in the vinyl aromatic compound and a long duration of efficiency into each of the distillation vessels of a conventional distillation apparatus in an amount sufficient to prevent polymerization therein.

U.S. Pat. No. 4,665,185 discloses a process for the efficient preparation of nitroxyls of sterically hindered amines by the oxidation of the amine using a hydroperoxide in the presence of a small amount of a metal ion catalyst, at moderate temperature for a short period of time, to give the nitroxyl in high yield and purity.

U.S. Pat. No. 4,774,374 discloses a vinyl aromatic composition stabilized against polymerization comprising (a) a vinyl aromatic compound and (b) an effective amount of a stabilizer system in which the active ingredient consists essentially of an oxygenated species formed by the reaction of oxygen and an N-aryl-N'-alkyl-p-phenylenediamine. Also disclosed is a process for inhibiting the polymerization of vinyl aromatic compounds employing such an oxygenated species.

U.S. Pat. No. 5,254,760 teaches that the polymerization of a vinyl aromatic compound, such as styrene, is very effectively inhibited during distillation or purification by the presence of at least one stable nitroxyl compound together with at least one aromatic nitro compound.

U.S. Pat. Nos. 5,545,782 and 5,545,786 disclose that nitroxyl inhibitors in combination with some oxygen reduce the premature polymerization of vinyl aromatic monomers during the manufacturing processes for such monomers. Even small quantities of air used in combination with the nitroxyl inhibitors are said to result in vastly prolonged inhibition times for the monomers.

U.S. Pat. No. 5,711,767 discloses that the use of nitroxide compounds alone or in combination with aromatic amines, such as substituted phenylenediamines, or phenolic antioxidants provides an effective way to prevent oxidative degradation and gum formation in gasolines.

U.S. Pat. No. 5,907,071 discloses that the polymerization of vinyl aromatic monomers such as styrene is inhibited by the addition of a composition of a stable hindered nitroxyl radical and an oxime compound.

U.S. Pat. No. 5,910,232 teaches that inhibition performance in styrene processing is improved through the addition of a stable nitroxide free radical compound to the styrene feed and to the reflux of at least one column. A non-toxic retarder, such as phenylenediamine, may also optionally be added to the styrene feed and to the reflux.

European Patent Application 0 178 168 A2 discloses a method for inhibiting the polymerization of an α,β-ethylenically unsaturated monocarboxylic acid during its recovery by distillation by using a nitroxide free radical.

European Patent Application 0 765 856 A1 discloses a stabilized acrylic acid composition in which the polymerization of the acrylic acid is inhibited during the distillation process for purifying or separating the acrylic acid as well as during transport and storage. The compositions comprise three components: (a) acrylic acid, (b) a stable nitroxyl radical, and (c) a dihetero-substituted benzene compound having at least one transferable hydrogen (e.g., a quinone derivative such as the monomethyl ether of hydroquinone (MEHQ)). During the distillation process, transport, and storage, components (b) and (c) are present in a polymerization-inhibiting amount. During the distillation process, oxygen (d) is preferably added with components (b) and (c).

WO 97/46504 concerns substance mixtures containing: (A) monomers containing vinyl groups; and (B) an active amount of a mixture which inhibits premature polymerization of the monomers containing vinyl groups during their purification or distillation and contains: (i) between 0.05 and 4.5 wt %, relative to the total mixture (B), of at least one N-oxyl compound of a secondary amine which has no hydrogen atom at the α-C atoms; and (ii) between 99.95 and 95.5 wt % relative to the total mixture (B), of at least one nitro compound. The publication also discloses a process for inhibiting the premature polymerization of monomers, and the use of mixture (B) for inhibiting the premature polymerizatin of monomers.

WO 98/14416 discloses that the polymerization of vinyl aromatic monomers such as styrene is inhibited by the addition of a composition of a stable hindered nitroxyl radical and an oxime compound.

WO 98/25872 concerns substance mixtures containing: (A) compounds containing vinyl groups; (B) an active amount of a mixture which inhibits premature polymerization of the compounds containing vinyl groups and contains: (i) at least one N-oxyl compound of a secondary amine which does not carry any hydrogen atoms on the α-carbon atoms; and (ii) at least one iron compound; (C) optionally nitro compounds; and (D) optionally co-stabilizers. The publication also discloses a process for inhibiting the premature polymerization of compounds (A) containing vinyl groups, and the use of (B) optionally mixed with nitro compounds (C) and/or co-stabilizers (D) for inhibiting the premature polymerization of radically polymerizable compounds and stabilizing organic materials against the harmful effect of radicals.

WO 99/20584 (U.S. Pat. No. 5,955,643) discloses that polymerization can be inhibited during the anaerobic production of styrene through the addition of a combination of a stable nitroxide free radical compound and a non-toxic phenylenediamine compound.

U.K. Patent Number 1,127,127 discloses that acrylic acid can be stabilized against polymerization by the addition thereto of a nitroxide having the essential skeletal structure:

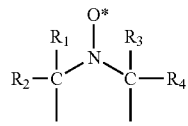

wherein $R_1$, $R_2$, $R_3$, and $R_4$ are alkyl groups and no hydrogen is bound to the remaining valencies on the carbon atoms bound to the nitrogen. The two remaining valencies that are not satisfied by $R_1$ to $R_4$ or nitrogen can also form part of a ring (e.g., 2,2,6,6 tetramethyl-4-hydroxy-piperidine-1-oxyl).

CS-260755 B1 is directed to the preparation of 4-substituted-2,2,6,6-tetramethylpiperidine nitroxyls as olefin stabilizers.

SU-334845 A1 is directed to the inhibition of the radical polymerization of oligoester acrylates using iminoxyl radical inhibitors of a given formula.

SU-478838 is directed to the inhibition of the radical polymerization of oligoester acrylates and the prevention of oligomeric peroxides using a binary polymerization inhibitor comprising quinone.

FR 2,761,060 relates to the prevention of premature polymerization of styrene during its production by dehydrogenation of ethylbenzene by injecting into the process effluent a radical inhibitor based on an oxyl-tetramethylpiperidine derivative.

The disclosures of the foregoing are incorporated herein by reference in their entirety.

SUMMARY OF THE INVENTION

As mentioned above, (a) nitroxyl compounds and (b) quinone methides are each known to be inhibitors or retarders of free radical polymerizations of unsaturated monomers. The present invention is directed to the discovery that the combination of at least one nitroxyl compound with at least one quinone alkide, preferably a quinone methide, having an electron withdrawing group at the 7-position provides better performance than either component alone, as indicated by both the low polymer numbers at steady state and the slow rate of polymerization after shutoff of feed in a steady state dynamic testing system.

More particularly, the present invention is directed to a method for inhibiting the premature polymerization of ethylenically unsaturated monomers comprising adding to said monomers an effective amount of:
A) at least one nitroxyl compound, and
B) at least one quinone alkide compound having an electron withdrawing group at the 7-position.

In another aspect, the present invention is directed to a composition comprising:
A) at least one nitroxyl compound, and
B) at least one quinone alkide compound having an electron-withdrawing group at the 7-position.

DESCRIPTION OF THE PREFERRED EMBODIMENTS

If a relatively small amount of a quinone alkide substituted with an electron withdrawing group at the 7-position (relative to the quantity necessary for its use alone) is added to a small amount of a nitroxyl compound (relative to the quantity necessary for its use alone), polymerization inhibition under normal usage conditions can be obtained that is equivalent to the use of the nitroxyl compound alone (indicated by wt % polymer at steady state in a reboiler test) and provides excellent protection in the event of a plant upset (indicated by slow polymer increase over time). This very effective inhibitor mixture is used at very reasonable dosages, providing an economically viable combination with enhanced performance characteristics.

The nitroxyl compounds that can be employed in combination with the quinone alkides in the practice of the present invention are preferably of the structure:

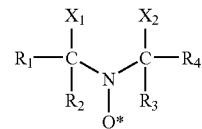

wherein $R_1$ and $R_4$ are independently selected from the group consisting of hydrogen, alkyl, and heteroatom-substituted alkyl and $R_2$ and $R_3$ are (1) independently selected from the group consisting of alkyl and heteroatom-substituted alkyl, or (2) taken together, form a ring structure with the nitrogen; and $X_1$ and $X_2$ (1) are independently selected from the group consisting of halogen, phosphorus (in any of it oxidation states), cyano, $COOR_7$, $-S-COR_7$, $-OCOR_7$, $-S-R_7$ (wherein $R_7$ is alkyl or aryl), amido, carbonyl, alkenyl, or alkyl of 1 to 15 carbon atoms, or (2) taken together, form a ring structure with the nitrogen.

In a particularly preferred embodiment, the nitroxyl compound has the structural formula:

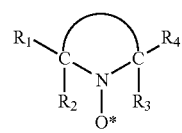

wherein $R_1$ and $R_4$ are independently selected from the group consisting of hydrogen, alkyl, and heteroatom-substituted alkyl and $R_2$ and $R_3$ are independently selected from the group consisting of alkyl and heteroatom-substituted alkyl, and the

portion represents the atoms necessary to form a five-, six-, or seven-membered heterocyclic ring.

Accordingly, one of the several classes of cyclic nitroxides that can be employed in the practice of the present invention can be represented by the following structural formula:

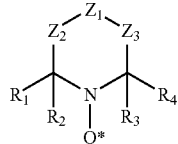

wherein $Z_1$, $Z_2$, and $Z_3$ are independently selected from the group consisting of oxygen, sulfur, secondary amines, tertiary amines, phosphorus of various oxidation states, and substituted or unsubstituted carbon atoms, such as >$CH_2$, >$CHCH_3$, >$C=O$, >$C(CH_3)_2$, >$CHBr$, >$CHCl$, >$CHI$, >$CHF$, >$CHOH$, >$CHCN$, >$C(OH)CN$, >$CHCOOH$, >$CHCOOCH_3$, >$CHCOOC_2H_5$, >$C(OH)COOC_2H_5$, >$C(OH)COOCH_3$, >$C(OH)CHOHC_2H_5$, >$CNR_5R_6$, >$CCONR_5R_6$, >$CH=NOH$, >$C=CH-C_6H_5$, >$CF_2$, >$CCl_2$, >$CBr_2$, >$CI_2$, >$CPR_{13}R_{14}R_{15}$, and the like, where $R_5$ and $R_6$ are independently selected from the group consisting of hydrogen, alkyl, aryl, and acyl and $R_{13}$, $R_{14}$, and $R_{15}$ are independently selected from the group consisting of unshared electrons, alkyl, aryl, $=O$, $OR_{16}$, and $NR_{17}R_{18}$, where $R_{16}$, $R_{17}$, and $R_{18}$ are independently selected from the group consisting of hydrogen, alkyl, and aryl. Where $R_5$ and/or $R_6$ are alkyl, it is preferred that they be a lower alkyl (i.e., one having one to four carbon atoms, e.g., methyl, ethyl, propyl, butyl, and isomers thereof).

Where $R_5$ and/or $R_6$ are aryl, it is preferred that they be aryl of from 6 to 10 carbon atoms, e.g., phenyl or naphthyl, which, in addition, may be substituted with noninterfering substituents, e.g., lower alkyl groups, halogens, and the like.

Where $R_5$ and/or $R_6$ are acyl, it is preferred that they be acyl of the structure

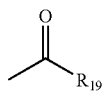

where $R_{19}$ is alkyl, aryl, $OR_{20}$, or $NR_{20}R_{21}$, and where $R_{20}$ and $R_{21}$ are alkyl, aryl, or

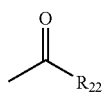

where $R_{22}$ is alkyl or aryl. Where $R_{19}$, $R_{20}$, $R_{21}$, or $R_{22}$ are alkyl, they are preferably alkyl of from 1 to 15 carbon atoms, more preferably lower alkyl of from one to four carbon atoms, as described above. Where $R_{19}$, $R_{20}$, $R_{21}$, or $R_{22}$ are aryl, they are preferably aryl of from 6 to 10 carbon atoms, as described above.

Another of the several classes of cyclic nitroxides that can be employed in the practice of the present invention can be represented by the following structural formula:

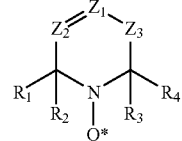

wherein $Z_1$, and $Z_2$, which may be the same or different, are nitrogen or substituted or unsubstituted carbon atoms, such as $=C(H)-$, $=C(CH_3)-$, $=C(COOH)-$, $=C(COOCH_3)-$, $=C(COOC_2H_5)-$, $=C(OH)-$, $=C(CN)-$, $=C(NR_5R_6)-$, $=C(CONR_5R_6)-$, and the like, and where $Z_3$, $R_5$, and $R_6$ are as described above.

The cyclic nitroxides employed in the practice of the present invention can also be derived from five-membered rings. These compounds are of the structure:

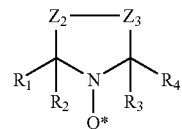

wherein $Z_2$ and $Z_3$, which may be the same or different, are sulfur, oxygen, secondary amines, tertiary amines, phosphorus of various oxidation states, or substituted or unsubstituted carbon atoms, such as >$CH_2$, >$CHCH_3$, >$C=O$, >$C(CH_3)_2$, >$CHBr$, >$CHCl$, >$CHI$, >$CHF$, >$CHOH$, >$CHCN$, >$C(OH)CN$, >$CHCOOH$, >$CHCOOCH_3$, >$CHCOOC_2H_5$, >$C(OH)COOC_2H_5$, >$C(OH)COOCH_3$, >$C(OH)CHOHC_2H_5$, >$CNR_5R_6$, >$CCONR_5R_6$, >$CH=NOH$, >$C=CH-C_6H_5$, $CF_2$, $CCl_2$, $CBr_2$, $CI_2$, >$CPR_{13}R_{14}R_{15}$, and the like, wherein the several R groups are as described above.

The cyclic nitroxides employed in the practice of the present invention can also have the structure:

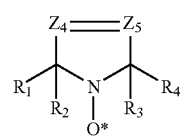

wherein $Z_4$ and $Z_5$, which can be the same or different, can be nitrogen or a substituted or unsubstituted carbon atom, such as $=C(H)-$, $=C(CH_3)-$, $=C(COOH)-$, $=C(COOCH_3)-$, $=C(COOC_2H_5)-$, $=C(OH)-$, $=C(CN)-$, $=C(NR_5R_6)-$, $=C(CONR_5R_6)-$, and the like, where $R_5$ and $R_6$ are as described above.

Another class of cyclic nitroxides that can be employed in the practice of the present invention is of the structure:

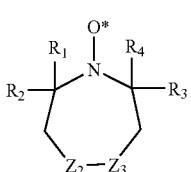

wherein $Z_2$ and $Z_3$, which may be the same or different, are sulfur, oxygen, secondary amines, tertiary amines, or substituted or unsubstituted carbon atoms, such as >CH$_2$, >CHCH$_3$, >C=O, >C(CH$_3$)$_2$, >CHBr, >CHCl, >CHI, >CHF, >CHOH, >CHCN, >C(OH)CN, >CHCOOH, >CHCOOCH$_3$, >CHCOOC$_2$H$_5$, >C(OH)COOC$_2$H$_5$, >C(OH)COOCH$_3$, >C(OH)CHOHC$_2$H$_5$, >CNR$_5$R$_6$, >CCONR$_5$R$_6$, >CH=NOH, >C=CH—C$_6$H$_5$, CF$_2$, CCl$_2$, CBr$_2$, CI$_2$, and the like, where R$_5$ and R$_6$ are as described above.

Further, two or more nitroxyl groups can be present in the same molecule, for example, by being linked through one or more of the Z-type moieties by a linking group E, as disclosed in U.S. Pat. No. 5,254,760, which is incorporated herein by reference.

As stated above, R$_1$ and R$_4$ are independently selected from the group consisting of hydrogen, alkyl, and heteroatom-substituted alkyl and R$_2$ and R$_3$ are independently selected from the group consisting of alkyl and heteroatom-substituted alkyl. The alkyl (or heteroatom-substituted alkyl) groups R$_1$ through R$_4$ can be the same or different and preferably contain 1 to 15 carbon atoms, e.g., methyl, ethyl, propyl, butyl, pentyl, hexyl, heptyl, octyl, nonyl, decyl, undecyl, dodecyl, tridecyl, tetradecyl, pentadecyl, and the like, and isomers thereof, e.g., t-butyl, 2-ethylhexyl, and the like. It is more preferred that R$_1$ through R$_4$ be independently selected lower alkyl (or heteroatom-substituted lower alkyl) of one to four carbon atoms (e.g., methyl, ethyl, propyl, butyl, and isomers thereof). Where heteroatom substituents are present, they can, for example, include halogen, oxygen, sulfur, nitrogen, and the like. It is most preferred that all of R$_1$ through R$_4$ be methyl.

Examples of suitable nitroxide free radical compounds that can be used in combination with the quinone alkide inhibitor in the practice of the present invention, include, but are not limited to:
2,2,6,6-tetramethyl-piperidinyloxy;
4-amino-2,2,6,6-tetramethyl-piperidinyloxy;
4-hydroxy-2,2,6,6-tetramethyl-piperidinyloxy;
4-oxo-2,2,6,6-tetramethyl-piperidinyloxy;
4-dimethylamino-2,2,6,6-tetramethyl-piperidinyloxy;
4-ethanoyloxy-2,2,6,6-tetramethyl-piperidinyloxy;
2,2,5,5-tetramethylpyrrolidinyloxy;
3-amino-2,2,5,5-tetramethylpyrrolidinyloxy;
2,2,4,4-tetramethyl-1-oxa-3-azacyclopentyl-3-oxy;
2,2,4,4-tetramethyl-1-oxa-3-pyrrolinyl-1-oxy-3-carboxylic acid;
2,2,3,3,5,5,6,6-octamethyl-1,4-diazacyclohexyl-1,4-dioxy;
4-bromo-2,2,6,6-tetramethyl-piperidinyloxy;
4-chloro-2,2,6,6-tetramethyl-piperidinyloxy;
4-iodo-2,2,6,6-tetramethyl-piperidinyloxy;
4-fluoro-2,2,6,6-tetramethyl-piperidinyloxy;
4-cyano-2,2,6,6-tetramethyl-piperidinyloxy;
4-carboxy-2,2,6,6-tetramethyl-piperidinyloxy;
4-carbomethoxy-2,2,6,6-tetramethyl-piperidinyloxy;
4-carbethoxy-2,2,6,6-tetramethyl-piperidinyloxy;
4-cyano-4-hydroxy-2,2,6,6-tetramethyl-piperidinyloxy;
4-methyl-2,2,6,6-tetramethyl-piperidinyloxy;
4-carbethoxy-4-hydroxy-2,2,6,6-tetramethyl-piperidinyloxy;
4-hydroxy-4-(1-hydroxypropyl)-2,2,6,6-tetramethyl-piperidinyloxy;
4-methyl-2,2,6,6-tetramethyl-1,2,5,6-tetrahydropyridine-1-oxyl;
4-carboxy-2,2,6,6-tetramethyl-1,2,5,6-tetrahydropyridine-1-oxyl;
4-carbomethoxy-2,2,6,6-tetramethyl-1,2,5,6-tetrahydropyridine-1-oxyl;
4-carbethoxy-2,2,6,6-tetramethyl-1,2,5,6-tetrahydropyridine-1-oxyl;
4-amino-2,2,6,6-tetramethyl-1,2,5,6-tetrahydropyridine-1-oxyl;
4-amido-2,2,6,6-tetramethyl-1,2,5,6-tetrahydropyridine-1-oxyl;
3,4-diketo-2,2,5,5-tetramethylpyrrolidinyloxy;
3-keto-4-oximino-2,2,5,5-tetramethylpyrrolidinyloxy;
3-keto-4-benzylidine-2,2,5,5-tetramethylpyrrolidinyloxy;
3-keto-4,4-dibromo-2,2,5,5-tetramethylpyrrolidinyloxy;
2,2,3,3,5,5-hexamethylpyrrolidinyloxy;
3-carboximido-2,2,5,5-tetramethylpyrrolidinyloxy;
3-oximino-2,2,5,5-tetramethylpyrrolidinyloxy;
3-hydroxy-2,2,5,5-tetramethylpyrrolidinyloxy;
3-cyano-3-hydroxy-2,2,5,5-tetramethylpyrrolidinyloxy;
3-carbomethoxy-3-hydroxy-2,2,5,5-tetramethylpyrrolidinyloxy;
3-carbethoxy-3-hydroxy-2,2,5,5-tetramethylpyrrolidinyloxy;
2,2,5,5-tetramethyl-3-carboxamido-2,5-dihydropyrrole-1-oxyl;
2,2,5,5-tetramethyl-3-amino-2,5-dihydropyrrole-1-oxyl;
2,2,5,5-tetramethyl-3-carbethoxy-2,5-dihydropyrrole-1-oxyl;
2,2,5,5-tetramethyl-3-cyano-2,5-dihydropyrrole-1-oxyl;
bis(1-oxyl-2,2,6,6-tetramethylpiperidin-4-yl)succinate;
bis(1-oxyl-2,2,6,6-tetramethylpiperidin-4-yl)adipate;
bis(1-oxyl-2,2,6,6-tetramethylpiperidin-4-yl)sebacate;
bis(1-oxyl-2,2,6,6-tetramethylpiperidin-4-yl)n-butylmalonate;
bis(1-oxyl-2,2,6,6-tetramethylpiperidin-4-yl)phthalate;
bis(1-oxyl-2,2,6,6-tetramethylpiperidin-4-yl)isophthalate;
bis(1-oxyl-2,2,6,6-tetramethylpiperidin-4-yl)terephthalate;
bis(1-oxyl-2,2,6,6-tetramethylpiperidin-4-yl)hexahydroterephthalate;
N,N'-bis(1-oxyl-2,2,6,6-tetramethylpiperidin-4-yl)adipamide;
N-(1-oxyl-2,2,6,6-tetramethylpiperidin-4-yl)-caprolactam;
N-(1-oxyl-2,2,6,6-tetramethylpiperidin-4-yl)-dodecylsuccinimide;
2,4,6-tris-[N-butyl-N-(1-oxyl-2,2,6,6-tetramethylpiperidin-4-yl)]-s-triazine;
4,4'-ethylenebis(1-oxyl-2,2,6,6-tetramethylpiperazin-3-one); and the like.

It is preferred that one member of the combination employed in the practice of the present invention be 4-amino-2,2,6,6-tetramethyl-piperidinyloxy (4-amino-TEMPO), 4-oxo-2,2,6,6-tetramethylpiperidinyloxy (4-oxo-TEMPO), 4-hydroxy-2,2,6,6-tetramethylpiperidinyloxy (4-hydroxy-TEMPO), or 2,2,6,6-tetramethyl-piperidinyloxy (TEMPO). Blends of two or more of the foregoing, e.g., 4-amino-TEMPO and 4-oxo-TEMPO, can also be employed.

Such stable nitroxide free radical compounds can be prepared by known methods. (See, for example, U.S. Pat. Nos. 3,163,677; 3,334,103; 3,372,182; 3,422,144; 3,494,930; 3,502,692; 3,873,564; 3,966,711; and 4,665,185; which are incorporated herein by reference.) They are suitable for use over a wide range of temperatures, but distillation temperatures employed with the ethylenically unsaturated monomers that are stabilized by the process of the present invention typically range from about 60° C. to about 180° C., preferably from about 70° C. to about 165° C., and, more preferably, from about 80° C. to about 150° C. Such distillations are generally performed at an absolute pressure in the range of about 10 to about 1,200 mm of Hg.

Quinone alkide compounds that are useful in the practice of the present invention include those disclosed in, for example, U.S. Pat. No. 5,583,247. More specifically, it is preferred that the quinone alkide be a compound of formula

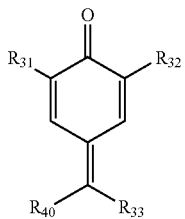

wherein:

$R_{31}$ and $R_{32}$ are independently alkyl of 4 to 18 carbon atoms, cycloalkyl of 5 to 12 carbon atoms or phenylalkyl of 7 to 15 carbon atoms, and $R_{33}$ is —CN, —COOH, —COOR$_{34}$, —COR$_{35}$, —OCOR$_{36}$, -CONR$_{37}$R$_{38}$ or —PO(OR$_{39}$)$_2$ where $R_{34}$ is alkyl of 1 to 18 carbon atoms, cycloalkyl of 5 to 12 carbon atoms, phenyl or benzyl, $R_{35}$ is alkyl of 1 to 18 carbon atoms, aryl of 6 to 10 carbon atoms or said aryl substituted by 1 or 2 alkyl of 1 to 4 carbon atoms or by hydroxyl, $R_{36}$ is alkyl of 1 to 18 carbon atoms, aryl of 6 to 10 carbon atoms or said aryl substituted by 1 or 2 alkyl of 1 to 4 carbon atoms or by hydroxyl, $R_{37}$ and $R_{38}$ are independently hydrogen, alkyl of 1 to 18 carbon atoms or said alkyl substituted by alkylamino of 1 to 4 carbon atoms, by dialkylamino of 2 to 8 carbon atoms or by hydroxyl; benzyl, aryl of 6 to 10 carbon atoms or said aryl substituted by alkyl of 1 to 4 carbon atoms, by alkylamino of 1 to 4 carbon atoms, by dialkylamino of 2 to 8 carbon atoms, by phenylamino or by hydroxyl, or —NR$_{37}$R$_{38}$ is morpholino, piperidino or pyrrolidino, $R_{39}$ is hydrogen or alkyl of 1 to 18 carbon atoms, and $R_{40}$ is hydrogen, alkyl, aryl, hydroxyl, alkoxy, —CN, —COOH, —COOR$_{34}$, —COR$_{35}$, —OCOR$_{36}$, —CONR$_{37}$R$_{38}$ or —PO(OR$_{39}$)$_2$.

Preferably, $R_{31}$, and $R_{32}$ are tert-butyl, tert-amyl, tert-octyl, cyclohexyl, α-methylbenzyl or α,α-dimethylbenzyl.

Most preferably, $R_{31}$, and $R_{32}$ are tert-butyl, tert-amyl or tert-octyl.

Preferably, $R_{33}$ is —CN, —COOH, —COOR$_{34}$, —COR$_{35}$, —OCOR$_{36}$, —CONR$_{37}$R$_{38}$ or —PO(OR$_{39}$)$_2$ wherein:

$R_{34}$ is alkyl of 1 to 8 carbon atoms, $R_{35}$ is methyl or phenyl, $R_{36}$ is alkyl of 1 to 18 carbon atoms or phenyl, $R_{37}$ and $R_{38}$ are independently hydrogen or alkyl of 1 to 18 carbon atoms, or —NR$_{37}$R$_{38}$ is morpholino or piperidino, and $R_{39}$ is alkyl of 1 to 4 carbon atoms.

Most preferably, $R_{33}$ is —CN, —COOH, —COOR$_{34}$, —COR$_{35}$, —OCOR$_{36}$, —CONR$_{37}$R$_{38}$ or —PO(OR$_{39}$)$_2$ wherein:

$R_{34}$ is alkyl of 1 to 4 carbon atoms, $R_{35}$ is methyl or phenyl, $R_{37}$ and $R_{38}$ are independently hydrogen or alkyl of 1 to 4 carbon atoms, or —NR$_{37}$R$_{38}$ is morpholino, and $R_{39}$ is alkyl of 1 to 4 carbon atoms.

Preferably, the quinone alkides of the present invention are selected from the group consisting of:

(3,5-di-tert-butyl-4-oxocyclohexa-2,5-dienylidene)acetonitrile, (3,5-di-tert-butyl-4-oxocyclohexa-2,5-dienylidene)acetic acid, (3,5-di-tert-amyl-4-oxocyclohexa-2,5-dienylidene)acetic acid, methyl(3,5-di-tert-butyl-4-oxocyclohexa-2,5-dienylidene) acetate, ethyl(3,5-di-tert-butyl-4-oxocyclohexa-2,5-dienylidene)acetate, n-butyl(3,5-di-tert-butyl-4-oxocyclohexa-2,5-dienylidene) acetate, 2,6-di-tert-butyl-4-(2-oxopropylidene)-cyclohexa-2,5-dienone, diethyl(3,5-di-tert-butyl-4-oxocyclohexa-2,5-dienylidene) methanephosphonate, (3,5-di-tert-butyl-4-oxocyclohexa-2,5-dienylidene)methyl acetate, (3,5-di-tert-butyl-4-oxocyclohexa-2,5-dienylidene)methyl pivalate, (3,5-di-tert-butyl-4-oxocyclohexa-2,5-dienylidene)methyl benzoate, and N,N-diethyl-2-(3,5-di-tert-butyl-4-oxocyclohexa-2,5-dienylidene)acetamide.

The quinone alkides of the present invention can, if desired, be combined with a 7-aryl quinone alkide, such as those described in U.S. Pat. No. 5,616,774. Preferably, such 7-aryl quinone alkides can be those of the formula:

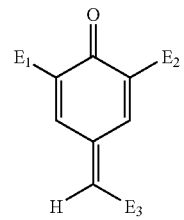

wherein $E_1$ and $E_2$ are independently alkyl of 4 to 18 carbon atoms, cycloalkyl of 5 to 12 carbon atoms or phenylalkyl of 7 to 15 carbon atoms, and $E_3$ is 2-, 3- or 4-pyridyl, 2- 3-thienyl, 2- 3-pyrryl, 2- 3-furyl, aryl of 6 to 10 carbon atoms, or said aryl substituted by one to three alkyl of 1 to 8 carbon atoms, alkoxy of 1 to 8 carbon atoms, alkylthio of 1 to 8 carbon atoms, alkylamino of 1 to 8 carbon atoms, dialkylamino of 2 to 8 carbon atoms, alkoxycarbonyl of 2 to 8 carbon atoms, hydroxy, nitro, amino, cyano, carboxy, aminocarbonyl, chloro or mixtures of said substituents.

Preferably such compounds are selected from the group consisting of:

2,6-di-tert-butyl-4-benzylidene-cyclohexa-2,5-dienone, 2,6-di-tert-butyl-4-(4-nitrobenzylidene)-cyclohexa-2,5-dienone, 2,6-di-tert-butyl-4-(3-nitrobenzylidene)-cyclohexa-2,5-dienone, 2,6-di-tert-butyl-4-(4-cyanobenzylidene)-cyclohexa-2,5-dienone, 2,6-di-tert-butyl-4-(4-dimethylaminobenzylidene)-cyclohexa-2,5-dienone, 2,6-di-tert-amyl-4-benzylidene-cyclohexa-2,5-dienone, 2,6-di-tert-butyl-4-(4-methoxybenzylidene)-cyclohexa-2,5-dienone, and 2,6-di-tert-butyl-4-(3,5-di-tert-butyl-4-hydroxybenzylidene)-cyclohexa-2,5- dienone.

The effective amount of the combination of (i) nitroxyl compound and (ii) quinone alkide compound is typically about 1 to 2,000 ppm, based on the weight of the ethylenically unsaturated monomer, although amounts outside this range may be appropriate depending upon the conditions of use. The amount of the combination of nitroxyl compound and quinone alkide is preferably about 5 to about 1,000 ppm, based on the weight of the ethylenically unsaturated monomer.

The preferred amounts of components (i) and (ii) are 1 to 99 percent by weight of component (i) and, correspondingly, 99 to 1 percent by weight of component (ii); more preferably, 20 to 80 percent by weight of component (i) and, correspondingly, 80 to 20 percent by weight of component (ii); and most preferably, 20-50 percent by weight of component (i) and 50-80 percent by weight of component (ii).

The inhibitor combination of the present invention is suitable for use over a wide range of temperatures, but distillation temperatures employed with the ethylenically unsaturated monomers that are stabilized by the process of the present invention typically range from about 60° C. to about 180° C., preferably from about 70° C. to about 165° C., and, more preferably, from about 80° C. to about 150° C. Such distillations are generally performed at an absolute pressure in the range of about 10 to about 1,200 mm of Hg.

The ethylenically unsaturated monomer, the premature polymerization of which is an object of the present invention, can be any such monomer for which unintended polymerization during its manufacture, storage, and/or distribution is a problem. Among those monomers that will benefit from the practice of the present invention are: styrene, α-methylstyrene, styrene sulfonic acid, vinyltoluene, divinylbenzenes, polyvinylbenzenes, alkylated styrene, 2-vinylpyridine, acrylonitrile, methacrylonitrile, methyl acrylate, ethyl acrylate, methyl methacrylate, ethyl methacrylate, acrylic acid, methacrylic acid, butadiene, chloroprene, isoprene, and the like.

The ethylenically unsaturated monomers will not necessarily be stabilized indefinitely by the presence of the inhibitor blend, especially when the monomers are heated as in distillation, but they can be considered to be stabilized as long as there is a measurable increase in the time for which they can be heated before the onset of polymerization in a static system and/or the amount of polymer made at constant temperature remains constant over time in a dynamic system.

Those skilled in the art will understand that, if desired, additional free radical scavengers can be included in the stabilized compositions. For example, air or $O_2$, as disclosed in U.S. Pat. Nos. 5,545,782 and 5,545,786, can be added, as can the aromatic nitro compounds disclosed in U.S. Pat. No. 5,254,760, the dihetero-substituted benzene compounds having at least one transferable hydrogen, e.g., a quinone derivative such as the mono-methyl-ether of hydroquinone disclosed in European Patent Application 0 765 856 A1, and other inhibitors, e.g., phenolics and certain inorganic salts, well-known to those skilled in the art.

The polymerization inhibitor composition can be introduced into the monomer to be protected by any conventional method. It can be added as a concentrated solution in suitable solvents just upstream from the point of desired application by any suitable means. For example, the individual inhibiting components can be injected separately or in combination to the monomer feed tank prior to injection into a distillation train. The individual inhibiting components can also be injected separately into the distillation train along with the incoming feed or through separate entry points, provided there is an efficient distribution of the inhibitors. Since the inhibitors are gradually depleted during the distillation operation, it is generally advantageous to maintain the appropriate amount of the inhibitor mixture in the distillation apparatus by adding inhibitors during the course of the distillation process. Adding inhibitors can be done either on a generally continuous basis or intermittently, in order to maintain the concentration of inhibitor mixture above the minimum required level.

The advantages and the important features of the present invention will be more apparent from the following examples.

EXAMPLES

Procedure for Dynamic Reboiler Test with Feed Shut-Off Preparation of Feed Solution.

T-Butylcatechol (TBC) is removed from commercially available styrene by distillation under vacuum. Removal of TBC is verified by caustic titration. The desired amount of inhibitor(s) is added to this TBC-free styrene either directly or by first making a concentrated solution of the inhibitor in TBC-free styrene followed by further dilution with TBC-free styrene.

Procedure for Reboiler Test.

A quantity of the Feed Solution containing inhibitor (blend) at the desired charge (stated as a wt/wt total inhibitor to styrene) is added to a round-bottom flask (the "Pot") and heated to the desired temperature (usually 116° C.) and brought to reflux by adjusting the pressure/vacuum. Once the Pot contents are at temperature, a continuous stream of fresh Feed Solution is begun at a rate that will add the volume of the initial Pot solution to the Pot over a period of time called the residence time (typically one hour). At the same time that the fresh Feed Solution flow is begun, the Bottoms Stream flow is also begun. The Bottoms Stream is solution in the Pot that is removed at the same rate as the fresh Feed Solution is added. The equal flows of Feed and Bottoms streams cause the quantity in the Pot to remain constant over the time of the experiment while allowing continuous replenishment of inhibitor. This procedure simulates the way inhibitors are used in a distillation train of a plant producing vinyl monomers. The experiment continues with flow in and out of the Pot for a specified period of time, typically seven hours. Samples are collected hourly from the Bottoms Stream. These samples are analyzed for polymer content via the methanol turbidity method. The amount of polymer in the samples is an indication of effectiveness of the inhibitor being tested. The lower the amount of polymer in the hourly samples, the more effective the inhibiting system should be during normal operation of a continuous manufacturing or purification process.

Procedure for Feed Shut-Off.

At the end of the Reboiler Test Run (typically seven hours), a sample is collected from the Bottoms Stream. This sample corresponds to Feed Shut-Off Time=0 minutes. The flows of fresh Feed Solution and Bottoms Stream are stopped. The vacuum and temperature are monitored and adjusted to maintain boiling at the desired temperature of the experiment. Samples are periodically removed from the Pot (typically every five minutes). These samples are analyzed for polymer content via the methanol turbidity method. A longer period of time before initiation of significant polymer formation is an indication of a more effective inhibiting system in the event of a loss of feed in the plant. Additionally, the lower the polymer number at a specific length of time after feed shut-off, the more effective the inhibitor system at providing protection for that length of time.

The results in Table 1 show that the performance of the combination of nitroxyl with quinone alkide is improved compared to either component alone in both steady state and feed shut-off tests. Thus, this blend should provide improved performance under both normal and upset operating conditions in a plant.

TABLE 1

| Inhibitor (Dose) | Steady State Polymer (wt %) | Polymer 50 minutes after Feed Shut-Off (wt %) |
|---|---|---|
| Nitroxyl (100 ppm) | 0.0003 | 4.2 |
| Nitroxyl (50 ppm) plus QM acid (262 ppm) | 0.0004 | 0.0006 |
| QM acid (350 ppm) | 0.0005 | 0.0017 |
| QM ester (150 ppm) | 0.49 | 4.66 |
| Nitroxyl (150 ppm) | 0.0053 | 2.52 |
| Nitroxyl (50 ppm) plus QM ester (100 ppm) | 0.0007 | 1.48 |

Nitroxyl is 4-oxo-TEMPO

QM acid is 3,5-di-t-butyl-4-oxo-cyclohexa-2,5-dienylidene acetic acid, the structure of which is

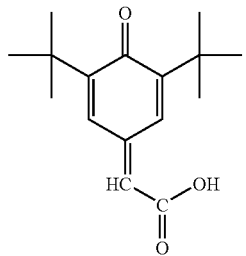

QM ester is ethyl 3,5-di-tert-butyl-4-oxo-cyclohexa-2,5-dienylidene acetate.

In view of the many changes and modifications that can be made without departing from principles underlying the invention, reference should be made to the appended claims for an understanding of the scope of the protection to be afforded the invention.

What is claimed is:

1. A composition comprising:
A) at least one nitroxyl compound of the structure:

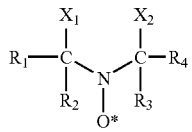

wherein $R_1$ and $R_4$ are independently selected from the group consisting of hydrogen, alkyl, and heteroatom-substituted alkyl and $R_2$ and $R_3$ are (1) independently selected from the group consisting of alkyl and heteroatom-substituted alkyl, or (2) taken together, form a ring structure with the nitrogen; and $X_1$ and $X_2$ (1) are independently selected from the group consisting of halogen, phosphorus (in any of its oxidation states), cyano, $COOR_7$, $-S-COR_7$, $-OCOR_7$, $-S-R_7$ (wherein $R_7$ is alkyl or aryl), amido, carbonyl, alkenyl, or alkyl of 1 to 15 carbon atoms, or (2) taken together, form a ring structure with the nitrogen, and B) at least one quinone alkide compound of the formula

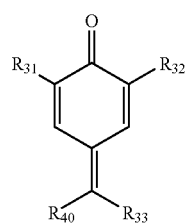

wherein:
$R_{31}$ and $R_{32}$ are independently alkyl of 4 to 18 carbon atoms, cycloalkyl of 5 to 12 carbon atoms or phenylalkyl of 7 to 15 carbon atoms, and
$R_{33}$ is $-CN$, $-COOH$, $-COOR_{34}$, $-COR_{35}$, $-OCOR_{36}$, $-CONR_{37}R_{38}$ or $-PO(OR_{39})_2$ where $R_{34}$ is alkyl of 1 to 18 carbon atoms, cycloalkyl of 5 to 12 carbon atoms, phenyl or benzyl,
$R_{35}$ is alkyl of 1 to 18 carbon atoms, aryl of 6 to 10 carbon atoms or said aryl substituted by 1 or 2 alkyl of 1 to 4 carbon atoms or by hydroxyl,
$R_{36}$ is alkyl of 1 to 18 carbon atoms, aryl of 6 to 10 carbon atoms or said aryl substituted by 1 or 2 alkyl of 1 to 4 carbon atoms or by hydroxyl,
$R_{37}$ and $R_{38}$ are independently hydrogen; alkyl of 1 to 18 carbon atoms; or said alkyl substituted by alkylamino of 1 to 4 carbon atoms, by dialkylamino of 2 to 8 carbon atoms or by hydroxyl; benzyl; aryl of 6 to 10 carbon atoms; or said aryl substituted by alkyl of 1 to 4 carbon atoms, by alkylamino of 1 to 4 carbon atoms, by dialkylamino of 2 to 8 carbon atoms, by phenylamino, or by hydroxyl; or
$-NR_{37}R_{38}$ is morpholino, piperidino or pyrrolidino,
$R_{39}$ is hydrogen or alkyl of 1 to 18 carbon atoms, and
$R_{40}$ is hydrogen, alkyl, aryl, hydroxyl, alkoxy, $-CN$, $-COOH$, $-COOR_{34}$, $-COR_{35}$, $-OCOR_{36}$, $-CONR_{37}R_{38}$ or $-PO(OR_{39})_2$.

2. The composition of claim 1 wherein the nitroxyl compound has the structural formula:

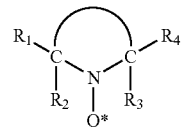

wherein $R_1$ and $R_4$ are independently selected from the group consisting of hydrogen, alkyl, and heteroatom-substituted alkyl and $R_2$, and $R_3$ are independently selected from the group consisting of alkyl and heteroatom-substituted alkyl, and the

portion represents the atoms necessary to form a five-, six-, or seven-membered heterocyclic ring.

3. The composition of claim 1 wherein the nitroxyl compound is selected from the group consisting of:
2,2,6,6-tetramethyl-piperidinyloxy;
4-amino-2,2,6,6-tetramethyl-piperidinyloxy;
4-hydroxy-2,2,6,6-tetramethyl-piperidinyloxy;
4-oxo-2,2,6,6-tetramethyl-piperidinyloxy;
4-dimethylamino-2,2,6,6-tetramethyl-piperidinyloxy;
4-ethanoyloxy-2,2,6,6-tetramethyl-piperidinyloxy;
2,2,5,5-tetramethylpyrrolidinyloxy;
3-amino-2,2,5,5-tetramethylpyrrolidinyloxy;
2,2,4,4-tetramethyl-1-oxa-3-azacyclopentyl-3-oxy;
2,2,4,4-tetramethyl-1-oxa-3-pyrrolinyl-1-oxy-3-carboxylic acid;
2,2,3,3,5,5,6,6-octamethyl-1,4-diazacyclohexyl-1,4-dioxy;
4-bromo-2,2,6,6-tetramethyl-piperidinyloxy;
4-chloro-2,2,6,6-tetramethyl-piperidinyloxy;

4-iodo-2,2,6,6-tetramethyl-piperidinyloxy;
4-fluoro-2,2,6,6-tetramethyl-piperidinyloxy;
4-cyano-2,2,6,6-tetramethyl-piperidinyloxy;
4-carboxy-2,2,6,6-tetramethyl-piperidinyloxy;
4-carbomethoxy-2,2,6,6-tetramethyl-piperidinyloxy;
4-carbethoxy-2,2,6,6-tetramethyl-piperidinyloxy;
4-cyano-4-hydroxy-2,2,6,6-tetramethyl-piperidinyloxy;
4-methyl-2,2,6,6-tetramethyl-piperidinyloxy;
4-carbethoxy-4-hydroxy-2,2,6,6-tetramethyl-piperidinyloxy;
4-hydroxy-4-(1-hydroxypropyl)-2,2,6,6-tetramethyl-piperidinyloxy;
4-methyl-2,2,6,6-tetramethyl-1,2,5,6-tetrahydropyridine-1-oxyl;
4-carboxy-2,2,6,6-tetramethyl-1,2,5,6-tetrahydropyridine-1-oxyl;
4-carbomethoxy-2,2,6,6-tetramethyl-1,2,5,6-tetrahydropyridine-1-oxyl;
4-carbethoxy-2,2,6,6-tetramethyl-1,2,5,6-tetrahydropyridine-1-oxyl;
4-amino-2,2,6,6-tetramethyl-1,2,5,6-tetrahydropyridine-1-oxyl;
4-amido-2,2,6,6-tetramethyl-1,2,5,6-tetrahydropyridine-1-oxyl;
3,4-diketo-2,2,5,5-tetramethylpyrrolidinyloxy;
3-keto-4-oximino-2,2,5,5-tetramethylpyrrolidinyloxy;
3-keto-4-benzylidine-2,2,5,5-tetramethylpyrrolidinyloxy;
3-keto-4,4-dibromo-2,2,5,5-tetramethylpyrrolidinyloxy;
2,2,3,3,5,5-hexamethylpyrrolidinyloxy;
3-carboximido-2,2,5,5-tetramethylpyrrolidinyloxy;
3-oximino-2,2,5,5-tetramethylpyrrolidinyloxy;
3-hydroxy-2,2,5,5-tetramethylpyrrolidinyloxy;
3-cyano-3-hydroxy-2,2,5,5-tetramethylpyrrolidinyloxy;
3-carbomethoxy-3-hydroxy-2,2,5,5-tetramethylpyrrolidinyloxy;
3-carbethoxy-3-hydroxy-2,2,5,5-tetramethylpyrrolidinyloxy;
2,2,5,5-tetramethyl-3-carboxamido-2,5-dihydropyrrole-1-oxyl;
2,2,5,5-tetramethyl-3-amino-2,5-dihydropyrrole-1-oxyl;
2,2,5,5-tetramethyl-3-carbethoxy-2,5-dihydropyrrole-1-oxyl;
2,2,5,5-tetramethyl-3-cyano-2,5-dihydropyrrole-1-oxyl;
bis(1-oxyl-2,2,6,6-tetramethylpiperidin-4-yl)succinate;
bis(1-oxyl-2,2,6,6-tetramethylpiperidin-4-yl)adipate;
bis(1-oxyl-2,2,6,6-tetramethylpiperidin-4-yl)sebacate;
bis(1-oxyl-2,2,6,6-tetramethylpiperidin-4-yl)n-butylmalonate;
bis(1-oxyl-2,2,6,6-tetramethylpiperidin-4-yl)phthalate;
bis(1-oxyl-2,2,6,6-tetramethylpiperidin-4-yl)isophthalate;
bis(1-oxyl-2,2,6,6-tetramethylpiperidin-4-yl)terephthalate;
bis(1-oxyl-2,2,6,6-tetramethylpiperidin-4-yl)hexahydroterephthalate;
N,N'-bis(1-oxyl-2,2,6,6-tetramethylpiperidin-4-yl)adipamide;
N-(1-oxyl-2,2,6,6-tetramethylpiperidin-4-yl)-caprolactam;
N-(1-oxyl-2,2,6,6-tetramethylpiperidin-4-yl)-dodecylsuccinimide;
2,4,6-tris-[N-butyl-N-(1-oxyl-2,2,6,6-tetramethylpiperidin-4-yl)]-s-triazine; and
4,4'-ethylenebis(1-oxyl-2,2,6,6-tetramethylpiperazin-3-one).

4. The composition of claim 1 wherein the quinone alkide is selected from the group consisting of:
(3,5-di-tert-butyl-4-oxocyclohexa-2,5-dienylidene)acetonitrile,
(3,5-di-tert-butyl-4-oxocyclohexa-2,5-dienylidene)acetic acid,
(3,5-di-tert-amyl-4-oxocyclohexa-2,5-dienylidene)acetic acid,
methyl (3,5-di-tert-butyl-4-oxocyclohexa-2,5-dienylidene)acetate,
ethyl (3,5-di-tert-butyl-4-oxocyclohexa-2,5-dienylidene)acetate,
n-butyl (3,5-di-tert-butyl-4-oxocyclohexa-2,5-dienylidene)acetate,
2,6-di-tert-butyl-4-(2-oxopropylidene)-cyclohexa-2,5-dienone,
diethyl (3,5-di-tert-butyl-4-oxocyclohexa-2,5-dienylidene)methanephosphonate,
(3,5-di-tert-butyl-4-oxocyclohexa-2,5-dienylidene)methyl acetate,
(3,5-di-tert-butyl-4-oxocyclohexa-2,5-dienylidene)methyl pivalate,
(3,5-di-tert-butyl-4-oxocyclohexa-2,5-dienylidene)methyl benzoate, and
N,N-diethyl-2-(3,5-di-tert-butyl-4-oxocyclohexa-2,5-dienylidene)acetamide.

5. The composition of claim 1 wherein the quinone alkide compound is 3,5-di-t-butyl-4-oxo-cyclohexa-2,5-dienylidene acetic acid.

6. The composition of claim 1 wherein the quinone alkide compound is an alkyl 3,5-di-t-butyl-4-oxo-cyclohexa-2,5-dienylidene acetic acid.

7. The composition of claim 1 wherein the nitroxyl compound is 4-oxo-2,2,6,6-tetramethyl piperidinyloxy.

8. The composition of claim 5 wherein the nitroxyl compound is 4-oxo-2,2,6,6-tetramethyl piperidinyloxy.

9. The composition of claim 6 wherein the nitroxyl compound is 4-oxo-2,2,6,6-tetramethyl piperidinyloxy.

* * * * *

UNITED STATES PATENT AND TRADEMARK OFFICE
CERTIFICATE OF CORRECTION

PATENT NO.       : 7,473,795 B2                                     Page 1 of 1
APPLICATION NO.  : 11/370691
DATED            : January 6, 2009
INVENTOR(S)      : Brigitte Benage It is certified that error appears in the above-identified patent and that said Letters Patent is hereby corrected as shown below:

Claim 6, Column 18, Lines 43-44, "alkyl 3,5-di-t-butyl-4-oxo-cyclohexa-2,5-dienylidene acetic acid" should read --alkyl 3,5-di-t-butyl-4-oxo-cyclohexa-2,5-dienylidene acetate--.

Signed and Sealed this

Twelfth Day of May, 2009

JOHN DOLL
*Acting Director of the United States Patent and Trademark Office*